United States Patent [19]
Skarky

[11] Patent Number: 6,135,768
[45] Date of Patent: *Oct. 24, 2000

[54] DENTAL DEVICE FOR POSITIONING THE MANDIBLE AND THE MAXILLA IN CENTRIC RELATION AND METHODS FOR USING SAME

[76] Inventor: Floyd E. Skarky, 6305 Waterford Blvd., Ste. 445, Oklahoma City, Okla. 73118

[ * ] Notice: This patent is subject to a terminal disclaimer.

[21] Appl. No.: 09/270,877

[22] Filed: Mar. 17, 1999

Related U.S. Application Data

[63] Continuation of application No. 08/784,097, Jan. 15, 1997, Pat. No. 5,954,503.

[51] Int. Cl.$^7$ ............................................. A61C 9/00
[52] U.S. Cl. ................................................ 433/71; 433/140
[58] Field of Search .................................. 433/6, 71, 140; 128/859, 861, 862

[56] References Cited

U.S. PATENT DOCUMENTS

| | | | |
|---|---|---|---|
| 2,694,397 | 11/1954 | Herms | 128/861 |
| 2,833,278 | 5/1958 | Ross | 128/862 |
| 3,478,429 | 11/1969 | Shilliday | 433/6 |
| 3,532,091 | 10/1970 | Lerman | 128/862 |
| 4,211,008 | 7/1980 | Lerman | 433/6 |
| 4,445,856 | 5/1984 | Sturtzkopf | 433/71 |
| 4,624,640 | 11/1986 | Tesini | 433/71 |
| 4,676,748 | 6/1987 | Pietkivitch | 433/71 |
| 5,082,007 | 1/1992 | Adell | 128/861 |
| 5,293,880 | 3/1994 | Levitt | 128/861 |
| 5,513,656 | 5/1996 | Boyd, Sr. | 433/6 |
| 5,954,503 | 9/1999 | Skarky | 433/71 |

OTHER PUBLICATIONS

Evaluation, Diagnosis, and Treatment of Occlusal Problems, by Peter Dawson, Second Edition, Copyright 1989, pp. 36, 37, 41, 42, 43, 44, 45, 46, 47, 168, 169, 170, 171, 172, 189, 190, 191, 192, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237.

Exhibit A is a photograph of a leaf gage which has been used by dentists in the past for attempting to position the maxilla and the madible in centric relation.

Exhibit B is a photograph of a device having two different hardness of way also has been used in the past in an attempt to establish centric relation between the maxilla and the madible.

Exhibit C is a photograph of a Lucia Jig which was a cap–like structure which was fitted over the upper and lower anterior teeth.

*Primary Examiner*—Ralph A. Lewis
*Attorney, Agent, or Firm*—Dunlap, Codding & Rogers, P.C.

[57] ABSTRACT

Methods are disclosed for making impressions of at least a portion of a patient's upper and lower posterior teeth with the patient's mandible and maxilla positioned in a centric relation, relieving muscle trismus and pain caused by muscles, diagnosing temporal mandibular joint problems in a patient, and positioning a patient's mandible and maxilla in a centric relation using a dental device sized and shaped so as to be inserted into the patient's mouth.

4 Claims, 2 Drawing Sheets

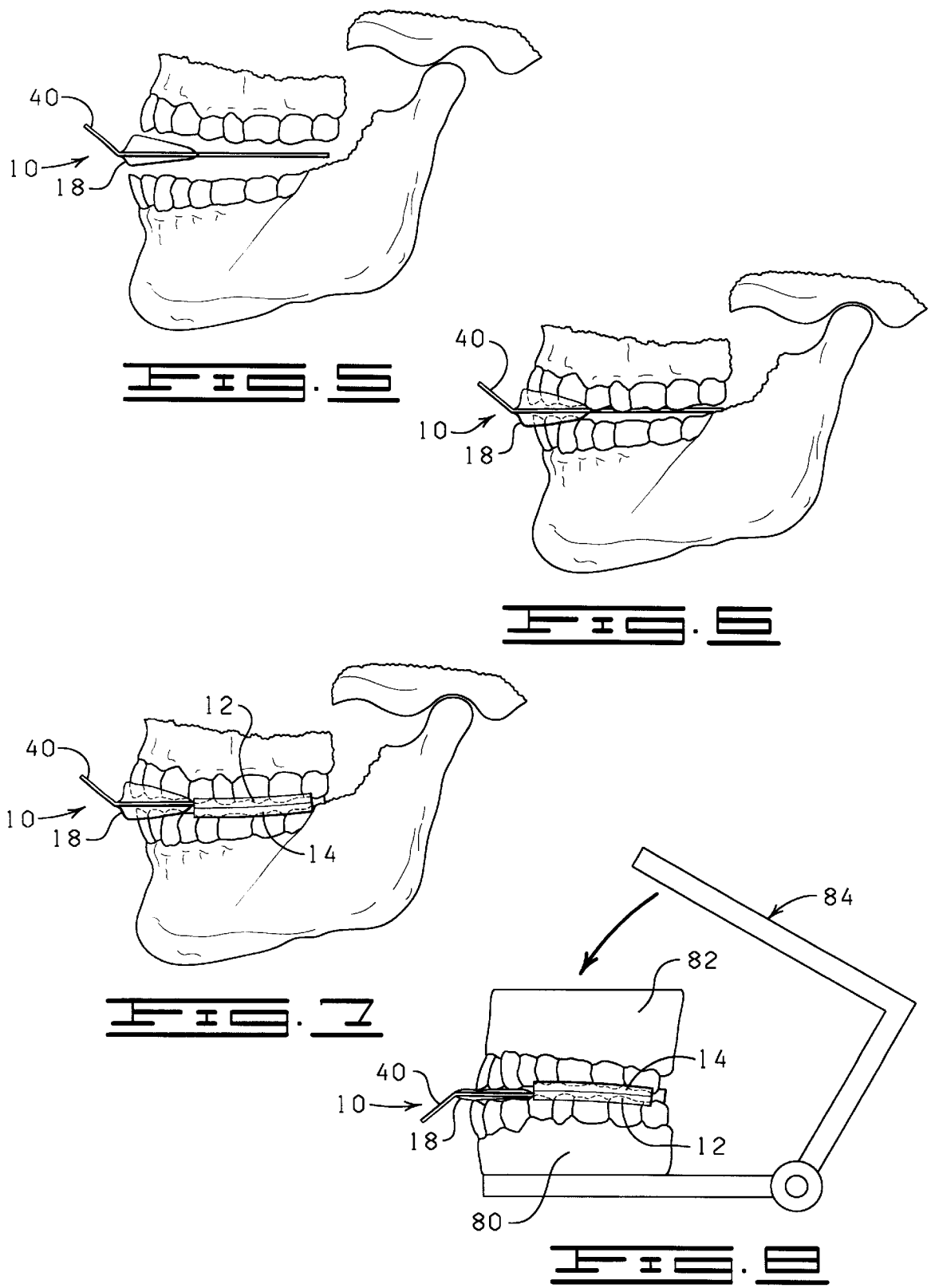

DENTAL DEVICE FOR POSITIONING THE MANDIBLE AND THE MAXILLA IN CENTRIC RELATION AND METHODS FOR USING SAME

CROSS-REFERENCE TO RELATED APPLICATIONS

This application is a continuation of U.S. Ser. No. 08/784,097, filed Jan. 15, 1997, now U.S. Pat. No. 5,954,503, entitled "DENTAL DEVICE FOR POSITIONING THE MANDIBLE AND THE MAXILLA IN CENTRIC RELATION AND METHODS FOR USING SAME".

STATEMENT REGARDING FEDERALLY SPONSORED RESEARCH OR DEVELOPMENT

Not applicable.

BACKGROUND OF THE INVENTION

Field of the Invention

The present invention relates generally to dental devices and, more particularly, but not by way of limitation, to a dental device for positioning the mandible and the maxilla in centric relation and methods for using same.

BRIEF DESCRIPTION OF THE SEVERAL VIEWS OF THE DRAWING

FIG. 5 is a diagrammatic, schematic view showing a portion of a maxilla and a portion of a mandible with the dental device of FIGS. 1 and 2 inserted between the upper and the lower teeth with the upper and the lower teeth shown in a partially opened positioned, the mandible and the maxilla not being in centric relation.

FIG. 6 is a view similar to FIG. 5, but showing the upper and the lower teeth in the closed position with the dental device of FIGS. 1 and 2 disposed therebetween, and the mandible and the maxilla in centric relation.

FIG. 7 is a view similar to FIGS. 5 and 6, but showing the dental device of FIGS. 3 and 4 disposed between the upper and the lower teeth with impression materials connected to the dental device and with the occlusal surfaces of the upper and lower posterior teeth engaging and impressing upon the impression materials, the mandible and the maxilla being in centric relation.

FIG. 8 is a schematic, diagrammatic view showing a portion of a typical articulator with a maxillary stone model mounted on the articulator with the dental device along with the impression material disposed on the occlusal surface of the maxillary stone model and showing the mandibular cast disposed on the impression materials and positioned thereon to position the maxilla and the mandible in centric relation, the mandibular cast being shown, prior to connecting the mandibular cast to the articulator.

DETAILED DESCRIPTION OF THE INVENTION

Figure 1:
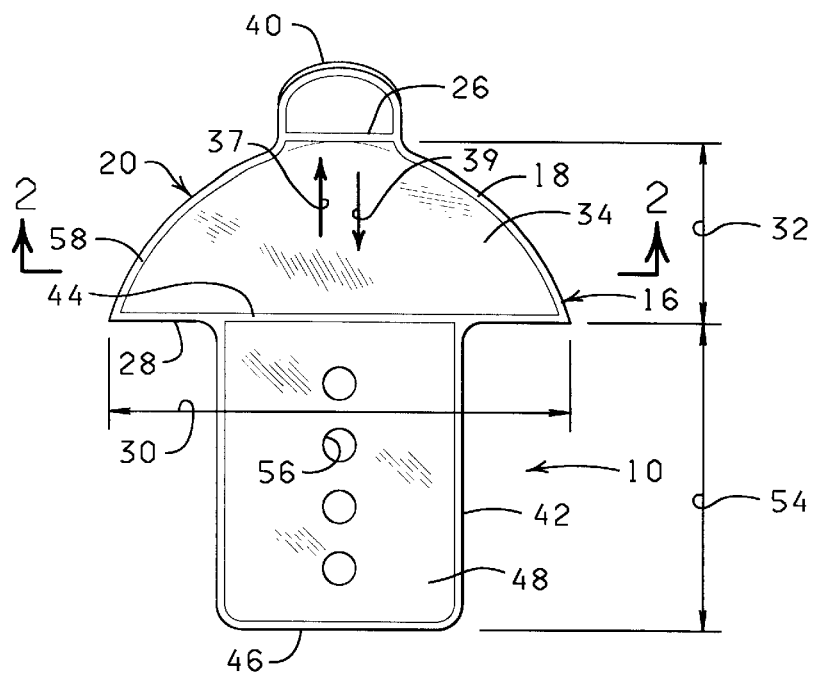
FIG. 1 is a top plan view of a dental device constructed in accordance with the present invention.
Figure 2:
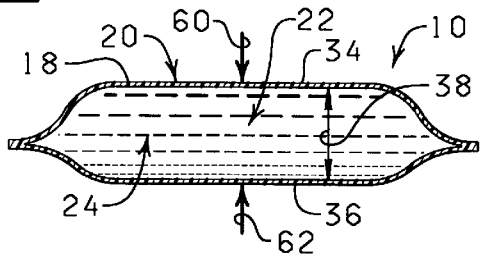
FIG. 2 is a cross-sectional view taken substantially along the lines 2—2 of FIG. 1.

Referring to the drawings in general and to FIGS. 1 and 2 in particular shown therein and designated by the general reference numeral 10 is a dental device constructed in accordance with the present invention. In one embodiment, the dental device 10 comprises a first and a second impression material 12 and 14 (shown in FIGS. 3 and 4).

The dental device 10 is constructed of materials, adapted, sized and shaped to be inserted into a patient's mouth generally between the patient's upper teeth and lower teeth for cooperating in positioning the mandible and the maxilla of the patient in centric relation. The term "centric relation" as used herein means the relationship of the mandible to the maxilla when the properly aligned condyle-disk assemblies are in the most superior position against the eminentia, irrespective of tooth position or vertical dimension. In this position, the head of the condyle of the mandible is in the upper most superior position in the glenoid fossa with a disk assembly between it and the eminentia. The term "centric relation" is well known to those skilled in the art of dentistry, and a more detailed description or illustrations are not deemed necessary.

An individual patient has two sets of muscles that control centric relation, a set of elevator muscles and a set of positioner muscle. The elevator muscles are the masseter, temporalis, medial, pterygoid and the positioner muscles are the lateral pterygoid, and anterior fibers of the temporalis. When one set of muscles fires, the other set of muscles should release. That is, when the elevator muscles fire, the positioner muscles release, and when the positioner muscles fire, the elevator muscles release. When this does not occur, then there is an in-coordination of the muscles of the masticatory system which can cause pain and destruction of the dentition.

The dental device 10 is constructed of materials, adapted, sized and shaped to program the upper and the lower arches back to their original position and not to the displaced position. That is, the dental device 10 is adapted to cooperate in positioning the mandible and the maxilla in centric relation.

Referring to FIGS. 1 and 2, the dental device 10 comprises a centric bite assembly 16 which is constructed of materials, shaped and sized for positioning in a patient's mouth generally between the upper and the lower anterior teeth while leaving the posterior teeth spaced a distance apart when the patient bites down on the centric bite assembly 16 with the anterior teeth engaging the centric bite assembly. At least portions of the centric bite assembly 16 are constructed of pliable material adapted to permit the lower anterior teeth to move relative to the upper anterior teeth when the patient bites down on the centric bite assembly 16 for cooperating in positioning the mandible and the maxilla in centric relation, as will be described in greater detail below.

The centric bite assembly 16 includes a bite portion 18 which is adapted, constructed of materials, sized and shaped so the patient can bite down on the bite portion 18 when the centric bite assembly 16 is positioned between the upper and the lower anterior teeth of the patient. The bite portion 18 in particular is constructed of pliable material so that when the patient bites down on the bite portion 18 with at least some of the patient's anterior teeth, the patient's posterior teeth are spaced a distance apart. In one preferred embodiment as shown in the drawings, the bite portion 18 comprises an arch shaped case 20 having a cavity 22 (FIG. 2) formed therein. The cavity 22 is filled with a cavity fill pliable material 24 (FIG. 2).

As shown in FIG. 1, the bite portion 18 has a first end 26 and a second end 28. The bite portion 18 is shaped in the form of an arch having a planar base forming the second end 28.

The second end 28 (base portion) has a length 30 (FIG. 1). A distance 32 (FIG. 1) extends between the first end 26 and the second end 28 of the case 20. The length 30 and the distance 32 are sized so that the bite portion 18 has an area which is sufficient to fit between at least some of the upper and the lower anterior teeth of a patient and sufficient so that, when the patient bites down on the bite portion 18, at least some of the patient's upper and lower anterior teeth engage the case 20, but the patient's upper and lower posterior teeth are spaced from the second end 28 of the bite portion 18 and do not engage the bite portion 18, the patient's posterior teeth being held in a spaced apart relationship.

The bite portion 18 has an upper surface 34 (FIGS. 1 and 2) and a lower surface 36 (FIG. 2). The cavity fill pliable material 24 fills the cavity 22 of the case 20 and holds the upper surface 34 spaced a distance 38 (FIG. 2) from the lower surface 36.

The case 20 also is constructed of a pliable material of a type which will yield resulting in a partial collapsing of the case 20 as the patient bites down on the case 20 and which will permit relative movement between the upper and the lower anterior teeth during the use of the dental device 10. The construction of the case 20 of a pliable material and the cavity fill pliable material 24 cooperate to provide the portions of the centric bite assembly 16 constructed of pliable material which is selected to be yieldable when the patient bites down on the bite portion 18 and permit relative movement of the upper and lower teeth as the patient bites down on the bite portion 18. The distance 38 and the amount of cavity fill pliable material 24 disposed in the cavity 22 are determined to be sufficient so that, when the patient bites down on the bite portion 18, the upper surface 34 of the bite portion 18 does not engage the lower surface 36 of the bite portion 18, but rather remains spaced a distance from the lower surface 36.

The case 20 also is constructed of a material which, not only cooperates with the cavity fill material 24 to permit the case 20 to partially collapse as the patient bites down on the bite portion 18, but also the case 20 is constructed of a material which permits the upper and lower anterior teeth to move or slide relative to each other in directions 37 and 39 (FIG. 1). More particularly, the occlusal surfaces of the lower anterior teeth slide in the direction 39 on the case 20 moving the mandible toward centric relation with the maxilla as the patient bites down on the bite portion 18.

The pliable cavity fill material 24 cooperates with the pliable material of the cast 20 so the sliding movement mentioned above is the result of the patient's natural muscle contraction and expansion on relaxation as the patient bites down on the bite portion 18 and not caused by the bite portion 18 per se. The bite portion 18 does not result in a ramping effect as the patient bites down on the bite portion 18 which would force relative movement of the lower teeth in the direction 39 since the bite portion 18 conforms to the patient's upper and lower anterior teeth as the patient bites down on the bite portion 18.

A tab 40 (FIGS. 1, 3 and 4) extends a distance from the first end 26 of the bite portion 18 and extends a distance angularly upwardly from the upper surface 34 of the case 20. The tab 40 is adapted to be gripped by an individual (dentist) for inserting and positioning the bite portion 18 in a patient's mouth during the use of the dental device 10, as will be described in greater detail below.

Figure 3:
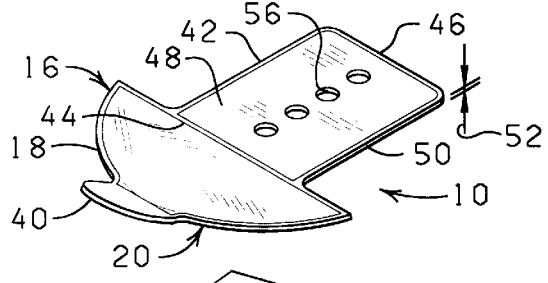
FIG. 3 is an exploded view showing the dental device of FIGS. 1 and 2 with impression materials aligned for positioning on the dental device.

The dental device 10 also includes an impression support 42 (FIGS. 1 and 3) having a first end 44 and a second end 46. The first end 44 is connected to the second end 28 of the bite portion 18 so as to extend substantially longitudinally therefrom substantially as shown in FIGS. 1 and 3. The impression support 42 extends a distance from the bite portion 18 terminating with the second end 46.

The impression support 42 has an upper impression support surface 48 (FIGS. 1 and 3) and a lower impression support surface 50 (FIG. 3). The upper and the lower impression support surfaces are spaced apart a distance 52 (FIG. 3). The upper and the lower impression support surfaces 48 and 50 preferably are planar and lie in parallel extending planes. A distance 54 (FIG. 1) extends between the first and the second ends 44 and 46 of the impression support 42.

As shown in FIGS. 1 and 3, a plurality of spaced apart openings 56 are formed through the impression support 42. Each of the openings 56 extends through the impression support 42 intersecting the upper and the lower impression support surfaces 48 and 50. Only one of the openings 56 is designated by a reference numeral in FIGS. 1 and 3 for clarity.

In one preferred embodiment, the dental device 10 is constructed of two sheets of 18 gauge polyurethane with one sheet disposed on top of the other and the two sheets are sealed together along the outer peripheral edges of the dental device 10, as indicated in FIG. 1 by the seal lines 58. The cavity fill material 24 and the cavity 22 are sealing enclosed via the case 20 along some of the seal lines 58. The two sheets are sealed together along the entire second end 28 of the bite portion 18 for forming the cavity 22 there between so the case 20 sealingly encloses the cavity 22.

In one embodiment, the cavity 22 was filled with a non-toxic gel of the type identified commercially as propylene glycol, commercially available from SAS Laboratories Incorporated, Newton, Mass. This embodiment of the dental device 10 had the following approximate dimensions: length 30 of about 5.8 cm; distance 32 of about 2.5 cm; distance 38 of about 0.8 cm; distance 52 of about 1.0 mm; distance 54 of about 3.8 cm.

The polyurethane sheets forming the bite portion 18 comprise the pliable material for the case 20 described above and the gel described above comprises the cavity fill pliable material 24. It should be noted that the case 20 may be constructed of any type of pliable material capable of performing the functions described herein and the cavity fill pliable material 24 may be any type of material such as the gel specifically identified above or a rubber or water or clay or cotton or any other type of pliable material suitable for performing the functions of the cavity fill pliable material 24, as described herein.

Although the bite portion 18 is shown as being arch shaped, the bite portion 18 may be any geometric shape so long as the bite portion 18 is shaped to be positioned between at least some of the upper and the lower anterior teeth of a patient and provide biting surfaces for the upper and lower anterior teeth. For example, the bite portion 18 may be rectangular shaped or somewhat triangular shaped.

The term "anterior teeth" generally refers to the cuspids and the intervening teeth therebetween. In one preferred embodiment, the bite portion 18 is shaped and sized to engage the anterior teeth from and including one cuspid to and including the other cuspid. It should be noted that the bite portion 18 could engage only the incisors and the intervening teeth or the bite portion 18 also could engage the lateral incisors and still perform the functions of the dental device 10 as described herein. It only is sufficient that the bite portion 18 be sized and shaped to engage at least some of the upper and lower anterior teeth of the patient for holding at least most of the anterior teeth spaced a distance apart while the patient bites downs on the bite portion 18 during the use of the dental device 10.

The dental device 10 is useful in at least three different applications. One recording centric relation, two relieving muscle trismus and pain and three diagnosing temporal mandibular joint problems.

For recording centric relation, the dentist grips the tab 40 of the dental device 10 and, while holding the tab 40, the dentist inserts the dental device 10 into the patient's mouth between the upper and the lower teeth to a position wherein the bite portion 18 is disposed between at least some of the upper and the lower anterior teeth of the patient, as generally shown in FIG. 5. The patient then bites down on the bite portion 18 with at least some of the patient's upper anterior teeth engaging the upper surface 34 of the case 20 and at least some of the patient's lower anterior teeth engaging the lower surface 36 of the case 20, as generally shown in FIG. 6.

In this position, the patient bites down on the bite portion 18 in general directions 60 and 62 (FIG. 2). As the patient's upper and lower anterior teeth engage the respective upper and lower surfaces 34 and 36 of the case 20 and as the patient bites down on the case 20 in the directions 60 and 62, the force of the patient's bite partially collapses the case 20 moving the upper and lower surfaces 34 and 36 of the case 20 generally in the directions 60 and 62 toward each other. Since the case 20 is constructed of a pliable material and since the cavity 22 is filled with the cavity fill pliable material 24, the case 20 generally collapses somewhat moving the upper surface 34 toward the lower surface 36 as the patient bites down on the bite portion 18 of the dental device 10.

The cavity fill pliable material 24 and the case 20 are constructed so that the cavity fill pliable material 24 always will support the upper surface spaced a distance from the lower surface of the case 20 as the patient bites down on the bite portion 18 and so the upper and the lower posterior teeth of the patient are spaced a distance apart when the patient has bitten down with full force on the bite portion 18 with a full power bite.

The term "power bite" as used herein means that the patient has bitten down on the bite portion 18 while at least some of the posterior teeth are held a distance apart by the bite portion 18 positioned between at least some of the anterior teeth. In this position, the muscles located behind the teeth then can contract, forcing the jaw into the centric relation position because there substantially are no posterior teeth touching or interfering with this movement.

The patient retains this power bite position for a period of time such as 5 or 20 minutes for example allowing or permitting the elevator muscles to center the condyle in centric relation while the positioner muscles relax thereby moving the mandible and the maxilla into centric relation.

After the mandible and the maxilla are positioned in centric relation, the patient opens the patient's mouth and the dentist removes the dental device from the patient's mouth. At this stage, it is important that the patient's mouth remains open leaving the mandible and the maxilla in centric relation. In other words, it is important at this stage that the patient not bite down and move the mandible and the maxilla out of centric relation. Preferably, the dentist will place a cotton roll between the anterior teeth of the patient to prevent the patient from closing the patient's mouth at this stage.

While the patient's mouth is maintained open or, in other words, while the patient's upper and lower teeth are maintained in a spaced apart relationship, the dentist then attaches the upper impression material 12 (FIGS. 3 and 4) to the upper impression support surface 48 of the impression support 42 and attaches a lower impression 14 (FIGS. 3 and 4) to the lower impression support surface 50 of the impression support 42.

Figure 4:
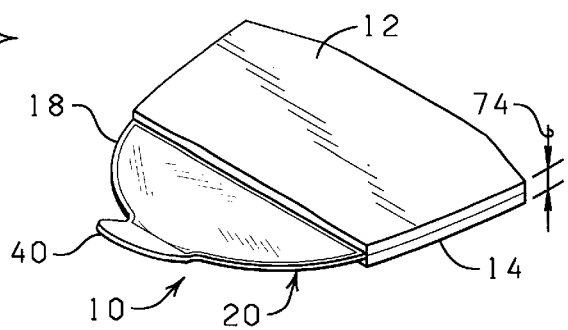
FIG. 4 is a perspective view showing the impression materials of FIG. 3 attached to the dental device of FIGS. 1 and 2 and comprising a portion thereof.

The upper and lower impression materials 12 and 14 are shown in FIG. 4 connected to the impression support 42 in FIG. 4. One preferred way of attaching the upper and the lower impression material 12 and 14 to the impression support 42 is to use an impression material of the type which is relative hard at room temperatures and pliable or relatively soft at elevated temperatures. One such impression material is of the type generally referred to as *BITE-REGISTRATION WAX* and commercially available from DeLar Corporation, Lake Oswego, Oreg. In one embodiment when using impression materials of this type, each impression material 12 and 14 had a thickness of about 2.5 mm giving an overall thickness of the two impression materials 12 and 14 of about 5 mm.

Using an impression material of the type described above for the upper and the lower impression materials 12 and 14, the dentist places the upper and the lower impression materials 12 and 14 in warm water or otherwise raises the temperature of the impression materials 12 and 14 so they soften. In this softened condition, the dentist places the upper impression material 12 on the upper impression support surface 48 and places a lower impression material 14 on the lower impression support surface 50 forcing the upper and the lower impression materials 12 and 14 toward each other and against the respective upper and the lower impression support surfaces 48 and 50.

While in this softened condition of the impression materials 12 and 14, the impression materials 12 and 14 tend to bind to the respective upper and lower impression support surface 48 and 50 thereby connecting the upper and lower impression materials 12 and 14 to the impression support 42 of the dental device 10. The openings 56 permit some of the impression materials 12 and 14 to flow into the openings 56 as the upper and the lower impression materials 12 and 14 are pressed against the impression support 42 thereby providing a more secure connection between the impression support 42 and the upper and lower impression materials 12 and 14.

The upper and lower impression materials 12 and 14 are sized and shaped and positioned on the dental device 10 to be positioned between the upper and lower posterior teeth of the patient when the dental device 10 is reinserted into the patient's mouth. As shown in FIGS. 3 and 4, the upper and the lower impression materials 12 and 14 are positioned near the second end 28 of the bite portion 18 and each of the impression materials 12 and 14 extends a distance from the bite portion 18 and may extend a distance form the second end 46 of the impression support 42 with the impression support 42 being disposed between the upper and the lower impression materials 12 and 14 and cooperating to provide the connection between the upper and the lower impression materials 12 and 14 and the bite portion 18. The impression support 42 has a thickness, that is, the distance 52 extending between the upper impression support surface 48 and the lower impression support surface 50. This distance 52 is determined along with the thickness of the impression materials 12 and 14 to be of a sufficient size so that, when the patient bites down on the bite portion 18, the patient's upper and lower posterior teeth will engage and make a sufficient impression in the impression materials 12 and 14.

When the softened impression materials 12 and 14 are placed adjacent the impression support 42 and pressed into position on the impression support 42, the impression support 42 impresses an impression of the impression support 42 in the impression materials 12 and 14. Thus, in a connected position, the impression materials 12 and 14 are disposed about adjacent each other and the upper impression material 12 is connected to the lower impression material 14.

The impression materials 12 and 14 have an overall thickness 74 (FIG. 4) which is about the same as the distance 38 (FIG. 2) between the upper and the lower surfaces of the bite portion 18. In any event, the impression materials 12 and 14 are sized and selected so that, when positioned on the impression support 42 and when the dental device 10 is inserted into the patient's mouth, the patient's upper and lower posterior teeth will engage and make impressions on the impression materials 12 and 14 as the patient bites down on the bite portion 18 in the manner described herein.

After the upper and the lower impression materials 12 and 14 have been connected to the impression support 42 and while the upper and the lower impression materials 12 and 14 still are in the softened condition, the dentist removes the roll of cotton from the patient's mouth and while maintaining the upper and the lower teeth spaced a distance apart, the dentist reinserts the dental device 10 into the patient's mouth and positions the bite portion 18 between at least some of the upper and lower anterior teeth thereby positioning the upper and the lower impression materials 12 and 14 generally between some of the patient's upper and lower posterior teeth. In this position of the dental device 10, the patient bites down on the dental device 10, as shown in FIG. 7. As the patient bites down on the dental device 10, at least some of the patient's upper and lower anterior teeth engage the bite portion 18 in the manner described before and at least some (preferably all) of the patient's upper and lower posterior teeth engage the respective upper and the lower impression materials 12 and 14. As the patient bites down on the dental device 10, the dentist may hold the patient's jaw to maintain centric relation if the patient tends to move the jaw forward out of centric relation.

As the patient's occulsal surfaces of the upper and lower posterior teeth engage the respective upper and the lower impression material 12 and 14, the engagement results in an impression of portions of the upper and the lower posterior teeth of the patient being made in the respective impression materials 12 and 14. During this stage, the patient should bite down on the bite portion 18 and the impression materials 12 and 14 as hard as practically possible to make clear impressions and impressions which are of a sufficient depth.

After the impressions have been made in the impression materials 12 and 14, the impression materials 12 and 14 then are cooled (hardened) by the dentist using cool water sprayed on the impression materials 12 and 14 for example while the dental device 10 including the impression materials 12 and 14 still are in the patient's mouth. After the impression materials 12 and 14 have been hardened, the dental device 10 including the impression materials 12 and 14 connected thereto are removed from the patient's mouth. The impression materials 12 and 14 then contain an impression of the patient's upper and lower anterior teeth with the patient's mandible and maxilla in centric relation.

The dental device 10 including the impressions of the upper and lower posterior teeth in the impression materials 12 and 14 then is used to position a maxillary stone model 80 (FIG. 8) and a mandibular cast 82 (FIG. 8) in proper relationship on an articulator 84 (FIGS. 6, 7 and 8) for use by the dentist in various reconstructive procedures.

First, the dentist, using any sharp instrument (not shown), makes a cut in the case 20 providing access to the cavity 22. At least a substantial portion of the cavity fill material 24 then is removed from the cavity 20. This will permit occlusal surfaces of the anterior teeth on the maxillary stone model 80 and the mandibular cast 82 to somewhat engage with only the materials forming the case 20 being disposed therebetween, as illustrated in FIG. 8.

Articulators and their use with maxillary stone models and mandibular casts are well known in the art of dentistry and a detailed description of the construction and use of such is not deemed necessary. In FIG. 8, the articulator 84 is shown only as typical representation of any articulator and is not intended to represent any particular articulator.

At this stage, the dentist already has made the maxillary stone model 80 and the mandibular cast 82 for the particular patient. The maxillary stone model 80 initially is mounted with a facebow on the articulator 84.

The articulator 84 then is turned upside down to the position shown in FIG. 8 with the maxillary stone model 80 under the mandibular cast 82. The dental device 10 is positioned on the maxillary stone model 80 with the impressions of the upper posterior teeth in the upper impression material 12 positioned in the occlusal surfaces of the upper posterior teeth of the maxillary stone model 80. The occlusal surfaces of the mandibular cast 82 then are positioned in the impressions of the lower posterior teeth in the lower impression material 14 thereby positioning the mandibular cast 82 and the maxillary stone model 80 in a true centric relation, in the position shown in FIG. 8.

The mandibular cast 82 then is secured or mounted (not shown) to the articulator 84 in this position. The mandibular cast 82 and the maxillary stone model 80 are now positioned on the articulator 84 in a true centric relation determined by the contracted elevator muscles, the relaxed positioner muscles and the condyle placed in the apex of force all determined by the particular patient.

As mentioned before, the dental device 10 also can be used to relieve muscle trismus and pain. The impression support 42 and the impression materials 12 and 14 are not necessary for the procedure, although the impression support 42 may be included on the dental device 10, if desired. For this procedure, the dental device 10 is positioned in the patient's mouth in a position wherein the bite portion 18 is positioned between at least some of the patient's anterior upper and lower teeth in the same manner as described before. The patient then bites down on the bite portion 18 with the anterior teeth engaging the bite portion 18 and providing forces in directions 60 and 62 on the bite portion 18 partially collapsing the upper and lower surfaces 34 and 36 in the directions 60 and 62 generally toward each other, in the same manner as described before. As the patient bites down on the bite portion 18 and as this position is maintained for a period of time, the mandible and the maxilla are moved into centric relation in the manner described before with the elevator muscles contracting and the positioner muscles relaxing. In this position, pain caused by the muscles, subsides.

Also, as mentioned before, the dental device 10 is useful in diagnosing temporal mandibular joint problems. The impression support 42 and the impression materials 12 and 14 are not necessary for the procedure, although the impression support 42 may be included on the dental device 10 if desired. With this procedure, the dental device 10 is positioned in the patient's mouth in the manner described before with the bite portion 18 generally positioned between at least some of the patient's upper and lower anterior teeth. In this position, the patient bites down on the bite portion 18 as hard as possible. While the patient bites down on the bite portion 18, if the disk has been displaced forward, the head of the condyle will be compressing the distal ligament, nerve endings and blood vessels against the eminences causing pain. Thus, the dentist can determine that it is a displaced disk causing the problem and it is not a muscle problem. On the other hand, if the disk is between the head of the condyle and eminence and the biting down causes no pain, the dentist knows it is a muscle problem.

As described herein, the dental device 10 is used to relax the muscles so that the condyle will set in the centric relation position. The dental device 10 allows the mandible to adjust to the position of centric relation as the muscles relax. The dental device 10 does not have a ramp effect that would cause the mandible to distalize or, in other words, to go too far back, posteriorly. The dental device 10 does not require customized appliances to be made for each patient. The dental device 10 is quick and simple and one bite fits all patients. The dental device 10 is a one piece device when the upper and the lower impression materials 12 and 14 are connected to the bite portion 18 and does not come in two pieces when being used by the dentist.

As described herein, the bite portion 18 comprised the case 20 with cavity fill material 24 disposed in the cavity 22. Rather than the dentist cutting the case 20 and forcing some of the cavity fill material 24 out of the case 20 during some of the operations as described herein, the dentist could simply cut the bite portion 18 from the impression support 42, thereby leaving the impression support 42 with the impression materials 12 and 14 connected thereto for use with the articulator 84 in the manner described before. Also, it should be noted that the bite portion 18 could be one solid piece constructed of a pliable material, rather than a case with a cavity fill with cavity fill material. In this last mentioned embodiment, the bite portion would be cut and removed from the impression support 42 with the impression materials 12 and 14 connected thereto for use with the articulator 84 in the manners described before.

Changes may be made in the construction and the operation of the various components, elements and assemblies described herein and changes may be made in the steps or the sequence of steps of the methods described herein without departing from the spirit and scope of the invention as defined in the following claims.

What is claimed:

1. A method for making impressions of at least a portion of a patient's upper and lower posterior teeth with the patient's mandible and maxilla positioned in a centric relation, comprising the steps of:

providing a pliable centric bite assembly sized and shaped to be positioned in the patient's mouth generally between at least a portion of the patient's upper and lower anterior teeth, the pliable centric bite assembly having an upper surface and a lower surface, the lower surface spaced a distance from the upper surface and the lower surface being slidably movable relative to the upper surface;

positioning the pliable centric bite assembly in the patient's mouth such that the pliable centric bite assembly is disposed between at least a portion of the patient's upper and lower anterior teeth;

biting, by the patient, on the pliable centric bite assembly with at least a portion of the patient's upper and lower anterior teeth bitingly contacting the upper surface and the lower surface of the pliable centric bite assembly, respectively, and thereby maintaining the patient's upper and lower posterior teeth spaced a distance apart as the patient bites down on the pliable centric bite assembly while permitting the lower anterior teeth to move relative to the upper anterior teeth, without causing a substantial ramping effect, and thereby positioning the mandibular and maxilla in centric relation;

maintaining the patient biting down on the pliable centric bite assembly for a period of time sufficient for the mandible and maxilla to move into centric relation;

removing the pliable centric bite assembly from the patient's mouth;

reinserting the pliable centric bite assembly and inserting an impression material into the patient's mouth such that the impression material is positioned between at least a portion of the patient's upper and lower posterior teeth while the pliable centric bite assembly is positioned between at least a portion of the patient's upper and lower anterior teeth;

biting, by the patient, on the pliable centric bite assembly with at least a portion of the patient's upper and lower anterior teeth whereby at least a portion of the patient's upper and lower posterior teeth bitingly engage the impression material and thereby form impressions of the patient's upper and lower posterior teeth; and removing the pliable centric bite assembly and the impression material from the patient's mouth thereby providing impressions of at least a portion of the patient's upper and lower posterior teeth in the impression material indicating the position of the patient's upper and lower posterior teeth when the patient's mandible and maxilla are positioned in centric relation.

2. A method for relieving muscle trismus and pain caused by muscles, comprising the steps of:

providing a pliable centric bite assembly positionable in the patient's mouth generally between at least a portion of the patient's upper and lower anterior teeth so as to maintain the patient's upper and lower posterior teeth spaced a distance apart as the patient bites down on the pliable centric bite assembly with at least a portion of the patient's upper and lower anterior teeth, the pliable centric bite assembly having an upper surface and a lower surface, the lower surface spaced a distance from the upper surface and the lower surface being slidably movable relative to the upper surface;

positioning the pliable centric bite assembly in the patient's mouth between at least a portion of the patient's upper and lower anterior teeth;

biting, by the patient, on the pliable centric bite assembly with at least a portion of the patient's upper and lower anterior teeth bitingly contacting the upper surface and the lower surface of the pliable centric bite assembly, respectively, whereby the pliable centric bite assembly maintains the patient's upper and lower posterior teeth spaced a distance apart and permits the lower anterior teeth to move relative to the upper anterior teeth, without causing a substantially ramping effect, and thereby cooperates in positioning the mandibular and maxilla in centric relation as the patient bites down on the pliable centric bite assembly with at least a portion of the patient's upper and lower anterior teeth, so that the patient's elevator muscles contract and the patient's positioner muscles relax resulting in a subsiding of the pain.

3. A method for diagnosing temporal mandibular joint problems in a patient, comprising the steps of:

providing a pliable centric bite assembly sized and shaped to be positionable in the patient's mouth for maintaining the patient's upper and lower posterior teeth spaced a distance apart as the patient bites down on the pliable centric bite assembly, the pliable centric bite assembly having an upper surface and a lower surface, the lower surface spaced a distance from the upper surface and the lower surface being slidably movable relative to the upper surface;

positioning the pliable centric bite assembly in the patient's mouth between at least a portion of the patient's upper and lower anterior teeth;

biting, by the patient, on the pliable centric bite assembly with at least a portion of the patient's upper and lower anterior teeth bitingly contacting the upper surface and the lower surface of the pliable centric bite assembly, respectively, so as to maintain the patient's upper and lower posterior teeth spaced a distance apart and thereby permit the lower anterior teeth to move relative to the upper anterior teeth, without causing a substantial ramping effect, whereby the patient's mandibular and maxilla are positioned in centric relation as the patient bites down on the pliable centric bite assembly with at least a portion of the patient's upper and lower anterior teeth, so that when the disk of the temporal mandibular joint is displaced forward, the head of the condyle will compress the distal ligament, nerve endings and blood vessels against the eminences thereby causing pain indicating a displaced disk as the diagnosed problem, and when the disk of the temporal mandibular joint is between the head of the condyle and eminences and no pain is present, a muscle problem is indicated.

4. A method for positioning a patient's mandible and maxilla in a centric relation, comprising the steps of:

providing a pliable centric bite assembly, the pliable centric bite assembly having an upper surface and a lower surface, the lower spaced a distance from the upper surface and the lower surface being slidably movable relative to the upper surface;

positioning the pliable centric bite assembly in the patient's mouth such that the pliable centric bite assembly is disposed between at least a portion of the patient's upper and lower anterior teeth;

biting, by the patient, on the pliable centric bite assembly with at least a portion of the patient's upper and lower anterior teeth bitingly contacting the upper surface and the lower surface of the pliable centric bite assembly, respectively, and thereby maintain the patient's upper and lower posterior teeth spaced a distance apart while permitting the lower anterior teeth to move relative to the upper anterior teeth, without causing a substantial ramping effect, and thereby position the mandibular and maxilla in centric relation; and maintaining the patient biting down on the pliable centric bite assembly for a period of time sufficient for the mandible and maxilla to move into centric relation.

* * * * *